United States Patent [19]

Sotome

[11] Patent Number: 4,978,686

[45] Date of Patent: Dec. 18, 1990

[54] METHOD OF PROTECTING CROPS BY A NON-TOXIC COMPOSITION

[76] Inventor: Kiyoshi Sotome, 4-10, Setagaya 2-chome, Setagaya-ku, Tokyo, Japan

[21] Appl. No.: 469,723

[22] Filed: Jan. 24, 1990

Related U.S. Application Data

[63] Continuation of Ser. No. 179,333, Apr. 18, 1988, abandoned.

[30] Foreign Application Priority Data

Apr. 13, 1987 [JP] Japan .................................. 62-88950

[51] Int. Cl.$^5$ ............................................. A01N 35/00
[52] U.S. Cl. ...................................... 514/698; 514/701
[58] Field of Search ................................. 514/698, 701

[56] References Cited

U.S. PATENT DOCUMENTS 2,465,854  3/1949  Dorman et al. ...................... 514/702

FOREIGN PATENT DOCUMENTS 2529755   1/1984  France ................................. 514/701
60146804  2/1985  Japan .................................. 514/701

*Primary Examiner*—Allen J. Robinson
*Attorney, Agent, or Firm*—Armstrong, Nikaido, Marmelstein, Kubovcik & Murray

[57] ABSTRACT

Crops can effectively be protected from the attack of insect pests, microorganisms and pathogenic microbes by spraying thereon a non-toxic and stable composition comprising cinnamic aldehyde and an antioxidant in the form of an emulsion or powder.

11 Claims, No Drawings

METHOD OF PROTECTING CROPS BY A NON-TOXIC COMPOSITION

This application is a continuation of application Ser. No. 179,333 filed Apr. 18, 1988 now abandoned.

BACKGROUND OF THE INVENITON

1. Field of the Invention

This invention relates to a method of protecting crops and more particularly, it is concerned with a method of protecting crops, whereby the protecting effect can be maintained in stable manner for a long time by the use of a non-toxic and stable composition containing cinnamic aldehyde as a predominant component.

2. Description of the Prior Art

Cinnamic aldehyde is a non-toxic material described in the official document as a food additive, which is represented by the following chemical structural formula:

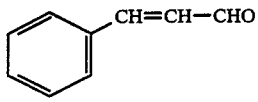

The inventor has noted that cinnamic aldehyde has an excellent microbe controlling effect and can favorably be applied to protection of crops and has thus proposed a method of protecting crops characterized by spraying an emulsion of cinnamic aldehyde on the crops and thus protecting the crops from insect pests, microorganisms and pathogenic microbes, as disclosed in Japanese Patent Publication No. 25682/1986. In this method, an emulsion of cinnamic aldehyde, for example, emulsified with a nonionic surfactant consisting of a condensate of ethylene oxide and propylene oxide is sprayed on crops to protect from molds such as ascomycetes, deuteromycetes, etc., pathogenic microbes such as phycomycetes, basidiomycetes, bacteria, etc. and insect pests such as cockroach carrying virus pathogenic microbes. This method is particularly effective for preventing economical loss due to damage by blight and noxious insects in the harvesting season for the health care of producers and for the preventive maintenance of soils.

Furthermore, the inventor has also proposed a method of protecting crops, characterized by applying a fertilizer with cinnamic aldehyde or a cinnamic aldehyde derivative to the soil, as disclosed in Japanese Patent Publication No. 32283/1986. This method is a novel and effective fertilizing method wherein the soil is fertilized with a fertilizer with cinnamic aldehyde or its derivative such as halogen derivatives thereof and thus subjected to disinfection in non-toxic manner while inhibiting harmful microbes without affecting useful bacteria, thereby maintaining a B/F value well-balanced.

Cinnamic aldehyde is a material which is non-toxic and has an excellent microbe controlling effect, but on the other hand, the stability of the microbe controlling effect is insufficient and the cause thereof has not been made clear, as described in Japanese Patent Application OPI (Kokai) No. 52236/1975 relating to a method of protecting foods with cinnamic aldehyde and a liquid bulb product. For the protection of crops, however, the stability of this effect for a long time has particularly been desired. Since cinnamic aldehyde has widely been used as a spice for foods, but has not been used for the protection of crops until the inventor has proposed, study of the stability for a long period of time has not been made.

SUMMARY OF THE INVENTION

It is an object of the present invention to provide a method of protecting crops using non-toxic cinnamic aldehyde, whereby a stable protecting effect can be obtained for a long time.

It is another object of the present invention to provide a method of protecting safely and economically crops using a novel composition containing cinnamic aldehyde, which is non-toxic and has an effect of selectively controlling or inhibiting only harmful microbes in the soil and selectively inhibiting the normal performance of Meloidogyne incognita, the effect being stably maintained.

These objects can be attained by a method of protecting crops, which comprises applying or spraying a composition comprising cinnamic aldehyde and an antioxidant on crops and thereby protecting the crops from insect pests, microorganism and microbes.

DETAILED DESCRIPTION OF THE INVENTION

The inventor has made studies on improvement of the stability of the protecting effect of cinnamic aldehyde when applied to crops and consequently, have found that the microbe inhibiting effect can be maintained by adding an antioxidant to cinnamic aldehyde to inhibit the oxidation of cinnamic aldehyde. The present invention is based on this finding.

Accordingly, the present invention provides a method of protecting crops against attack by pathogenic microbes and insect pests, which comprises applying or spraying a composition comprising cinnamic aldehyde and an antioxidant on crops and thereby protecting the crops therefrom.

In particularly preferred embodiments of the present invention, an emulsion comprising cinnamic aldehyde, an antioxidant and an emulsifier, or a composition comprising, on a support, cinnamic aldehyde and an antioxidant is used as the above described composition.

Various experiments relating to the protection of crops were carried out using the composition of the present invention, thus finding a surprising fact that the combination of cinnamic aldehyde and an antioxidant results in not only the above described antioxidant effect but also the following two large effects.

The first effect is a selective effect of inhibiting harmful microbes in the soil, i.e. pathogenic molds such as Fusarium, Pythium, Rhizoctonia, Phytophthora capsici, Pseudomonas and *Corticium rolfsii* without affecting useful microorganisms such as competitive yeasts, antinomycetes and useful molds.

The second effect is a breeding action of *Steinernema feltiae* having no damage on plant roots in spite of inhibiting the normal performance of *Meloidogyne incognita*. The second effect is suggestive of development of a new protecting method of crops utilizing the antibiosis by microorganism instead of disinfection of the soil with harmful chemical materials by forwarding the study.

Protection of crops by the use of the composition comprising cinnamic aldehyde and an antioxidant according to the present invention can be carried out by any of methods of irrigating the soil or spraying on plants, in which the parts or positions of the plant to be applied and the application time are not limited and the plant can wholly be treated, as will in detail be illustrated in the following Examples.

The composition of the present invention comprises cinnamic aldehyde and an antioxidant. As the antioxidant, there can be used various materials having oxidation inhibiting action, for example, vitamin E, n-propyl gallate, BHT, eugenol and the like. These materials are foods or additives for foods and accordingly particularly preferable from the standpoint of safety.

From the experimental results, it is preferred that the antioxidant is used in a proportion of 0.2 to 1% by weight to cinnamic aldehyde. In the case of eugenol capable of giving a sufficient oxidation inhibiting action in a proportion of at most 1%, in particular, the addition thereof in a proportion exceeding 1% is meaningless and it is rather found that such a higher concentration offsets the microbe inhibiting effect of cinnamic aldehyde.

The composition of the present invention is preferably in such a form as to be sprayed on crops in storage as well as practical use and it is more preferable to convert the composition into an emulsion or solid supported on a support, for example, powder or granules. The preferable embodiments of the present invention will now be illustrated in the case of an emulsion and solid.

The emulsion of the present invention can be prepared by adding water and an emulsifier to cinnamic aldehyde and an antioxidant and then homogenizing the resulting mixture. As the antioxidant for this emulsion, there can preferably be used vitamin E, n-propyl gallate, BHT, eugenol, etc. Above all, vitamin E has a higher oxidation inhibiting effect.

Useful examples of the emulsifier are those of anionic type such as fatty acid salts, higher alcohol sulfuric esters and alkylallylsulfonates; those of nonionic type such as polyoxyethylene alkyl ethers, polyoxyethylene alkylphenyl ethers, polyoxyethylene alkyl esters, polyoxyethylene sorbitan alkyl esters and sorbitan alkyl esters; and those of cationic type such as aliphatic amino salts, quaternary ammonium salts and alkylpyridinium salts. These emulsifiers can be used individually or in combination.

Preferably, the emulsion used in the present invention comprises 5 to 50% by weight of cinnamic aldehyde, 0.01 to 0.5% by weight of an antioxidant, 0.5 to 10% by weight of an emulsifier and the balance water. For practical use in a field, a reagent or preparation containing 5 to 50% by weight of cinnamic aldehyde is preferable.

Examples of the emulsion composition of the present invention are given in the following without limiting the present invention. L-64 and P-102 are condensates of polyoxyethylene-polyoxypropylene, commercially available as commercial names Pluronic L-64 and Pluronic P-102 manufactured by Asahi Denka Co., Ltd.

| Composition 1 | |
| --- | --- |
| Cinnamic Aldehyde | 400 g |
| Vitamine-E 80 | 4 g |
| L-64 | 50 g |
| P-102 | 50 g |
| Warm Water | 496 g |
| | 1000 g |
| Composition 2 | |
| Cinnamic Aldehyde | 200 g |
| BHT | 2 g |
| L-64 | 50 g |
| P-102 | 50 g |
| Warm Water | 698 g |
| | 1000 g |
| Composition 3 | |
| Cinnamic Aldehyde | 400 g |
| n-Propyl Gallate | 4 g |
| Polyoxyethylene Hardened Castor Oil | 50 g |
| Warm Water | 546 g |
| | 1000 g |
| Composition 4 | |
| Cinnamic Aldehyde | 200 g |
| Eugenol | 2 g |
| L-64 | 50 g |
| P-102 | 50 g |
| Warm Water | 698 g |
| | 1000 g |

The composition of solid type according to the present invention can be obtained by supporting cinnamic aldehyde and an antioxidant on a support. As the antioxidant, for example, there can be used vitamine E, BHT, n-propyl gallate, eugenol, etc. Above all, eugenol having a higher oxidation inhibiting effect is preferably used.

As the support of the present invention, there are for example used porous inorganic materials for adsorption, such as calcium oxide, silicon oxide, magnesium oxide, aluminum oxide, montmorillonite, bentonite, zeolite, white carbon, calcium silicate, etc. In particular, white carbon and calcium silicate are preferable. Calcium silicate fine powder is capable of adsorbing cinnamic aldehyde in an amount of four times as much as the weight of the fine powder, while white carbon adsorbes at most 1.5 times. In practical use in a field, the concentration of cinnamic aldehyde is 5 to 50% by weight. This concentration is sufficient and no higher concentration is required, so white carbon with a relatively low adsorptive capacity can sufficiently be used.

Examples of the solid composition of the present invention are given in the following without limiting the present invention.

| Composition 5 | |
| --- | --- |
| Cinnamic Aldehyde | 100 g |
| White Carbon | 200 g |
| Eugenol | 1 g |
| | 301 g |
| Composition 6 | |
| Cinnamic Aldehyde | 600 g |
| White Carbon | 394 g |
| Eugenol | 6 g |
| | 1000 g |
| Composition 7 | |
| Cinnamic Aldehyde | 300 g |
| White Carbon | 685 g |
| Eugenol | 15 g |
| | 1000 g |

Details of the action and advantages by the combination of cinnamic aldehyde and antioxidants, experiments relating to the effects of antioxidants, processes for the production of the composition according to the present invention and methods of applying the composition to crops will now be illutrated:

It is to be noted that there is a large difference in oxidation inhibiting effect between both the cases of using an emulsion composition and solid composition, even if using a same antioxidant. As is evident from the following results of Experiments 1 and 2 shown in Table 1 and Table 4, in the case of emulsions, the effects of vitamine E, BHT, n-propyl gallate and eugenol are higher, while in the case of solid compositions, eugenol shows a higher effect. That is, eugenol shows a higher oxidation inhibiting effect in both the cases and this effect is sufficient by the addition thereof in a proportion of 1% by weight to cinnamic aldehyde. The addition of more than 1% by weight is not only meaningless, but a higher concentration rather offsets the microbe inhibiting effect of cinnamic aldehyde. Vitamine E shows a higher oxidation inhibiting effect in the case of emulsions, but a lower effect in the case of solid compositions. Therefore, it is necessary to carefully select a suitable antioxidant depending on the type of the composition to be applied.

The following examples are given in order to illustrate the present invention in detail without limiting the same.

EXAMPLES

EXPERIMENT 1

1000 g of an emulsion comprising 200 g of cinnamic aldehyde, 40 g of a surfactant, 0.4 g of each of the following antioxidants (1) to (5) (0.2% by weight to cinnamic aldehyde) and the balance of water was prepared, while 1000 g of a comparative emulsion comprising 200 g of cinnamic aldehyde, 40 g of the surfactant and the balance of water, being free from the antioxidant, was prepared, As the antioxidant, there were used commercially available food additives, i.e. (1) dibutylhydroxytoluene (commercial name, BHT manufactured by Takeda Yakuhin Co., Ltd.), (2) licorice extract (commercial name, Sankanon manufactured by Maruzen Kasei Co., Ltd.), (3) vitamine E, (commercial name E-80, containing 80% of natural vitamine E, manufactured by Eisai Co., Ltd.) (4) n-propyl gallate (Wako Junyaku Co., Ltd.) and (5) L-ascorbyl stearate (Tokyo Kasei Co., Ltd.).

After the above described emulsions were allowed to stand at room temperature for 16 days, analysis of the components was carried out by gas chromatography to determine the oxidation inhibiting effects of the antioxidants (1) to (5) for cinnamic aldehyde. The purity of the cinnamic aldehyde used was 97.6% of cinnamic aldehyde and 0.4% of cinnamic acid, as a result of measurement by gas chromatography. The experimental results are as shown in Table 1, in which the order of the oxidation inhibiting effects from higher to lower is vitamin E, eugenol, n-propyl gallate and BHT, and Sankanon has little effect whereas L-ascorbyl stearate reversely promotes the oxidation.

TABLE 1

| Oxidation Inhibiting Effect of Cinnamic Aldehyde Emulsion (wt %) | | | |
|---|---|---|---|
| Antioxidant | Amount | Cinnamic Aldehyde | Cinnamic Acid |
| BHT | 0.2% | 95.8% | 1.2% |
| Sankanon | " | 71.4% | 21.0% |
| Vitamine E-80 | " | 97.2% | 0.4% |
| Eugenol | " | 96.8% | 0.8% |
| n-Propyl Gallate | " | 95.9% | 1.0% |
| L-Ascorbyl Stearate | " | 65.1% | 26.3% |
| Comparison | " | 70.4% | 20.1% |

EXAMPLE 1

Emulsion A of the present invention and antioxidant-free Emulsion B of the prior art were prepared by metering the following compositions and emulsifying by means of a homogenizer, based on the results of Experiment 1, and then subjected to a Schale test in a room, thus obtaining results as shown in Table 2.

| Composition of Emulsion A of the present invention (wt %) | |
|---|---|
| Cinnamic Aldehyde | 20 |
| BHT | 1 |
| Pluronic L-64 | 5 |
| Pluronic P-102 | 5 |
| Warm Water | 69 |
| Composition of Emulsion B of the Prior Art (wt %) | |
| Cinnamic Aldehyde | 20 |
| Pluronic L-64 | 5 |
| Pluronic P-102 | 5 |
| Warm Water | 70 |

Test culture media were prepared by adding Emulsions A and B to a PSA culture medium to give concentrations of 200 ppm and 400 ppm respectively, adequately shaking and pouring in petri dishes. PSA is the abbreviation for potato, sucrose and agar which is known as a potato culture medium. Each of microorganisms shown in Table 2 which had previously been cultured in other culture media was cut into 5 mm square and incubated in the center of the each solidified culture medium. Judgment of the effects of Emulsions A and B was carried out by subjecting the petri dishes for testing to culturing at 25° C. for 6 days and metering the growth diameter (mm) so as to know the growth inhibiting effect on the mycelial colony. A grown mycelial colony diameter of 70.0 mm, corresponding to the Schale with a diameter of 70 mm, means that the Schale was full of the mycelial colony.

Summarizing the results of Table 2, there was found no large difference before the passage of 6 days from the start of the test between Emulsions A and B, but the difference appeared and increased gradually with the passage of time and Emulsion B lost its effect 30 days after the start of the test as a result of the final test, whereas Emulsion A maintained its effect for the same time of period. These results apparently teach that according to the present invention, the oxidation of cinnamic aldehyde can effectively be prevented and the intrinsic microbe inhibiting effect thereof can be maintained.

TABLE 2

| Test of Microbe Inhibiting Effect of Cinnamic Aldehyde Emulsions A and B | | | | | | |
|---|---|---|---|---|---|---|
| Microbes Tested | Concentration of Emulsion | 6 days | 10 days | 15 days | 20 days | 30 days |
| Rizoctonia | A 200 ppm | — | — | — | 5.0 | 8.5 |
| solani | B 200 ppm | — | 16.0 | 26.0 | 50.8 | 70.0 |
|  | A 400 ppm | — | — | — | — | — |
|  | B 400 ppm | — | — | 17.0 | 39.0 | 70.0 |
| Pythium | A 200 ppm | — | — | — | — | — |
| debaryanum | B 200 ppm | — | 10.5 | 18.0 | 35.0 | 70.0 |
|  | A 400 ppm | — | — | — | — | — |
|  | B 400 ppm | — | — | 22.0 | 39.0 | 70.0 |
| Collectotri- | A 200 ppm | — | — | 6.0 | 10.1 | 22.0 |
| chum lagen- | B 200 ppm | 20.6 | 39.0 | 70.0 | 7.0 | 70.0 |
| arium | A 400 ppm | — | — | — | — | — |
|  | B 400 ppm | — | — | — | — | — |
| Fusarium o- | A 200 ppm | — | — | — | — | 7.8 |
| xysporum f, | B 200 ppm | — | 4.5 | 11.0 | 30.7 | 70.0 |

TABLE 2-continued

Test of Microbe Inhibiting Effect of Cinnamic Aldehyde Emulsions A and B

| Microbes Tested | Concentration of Emulsion | 6 days | 10 days | 15 days | 20 days | 30 days |
|---|---|---|---|---|---|---|
| cucumerinum | A 400 ppm | — | — | — | — | — |
|  | B 400 ppm | — | — | — | — | 10.0 |
| Botrytis cinerea | A 200 ppm | — | — | — | — | — |
|  | B 200 ppm | — | 10.2 | 40.5 | 70.0 | 70.0 |
|  | A 400 ppm | — | — | — | 8.0 | 30.0 |
|  | B 400 ppm | — | — | 16.5 | 70.0 | 70.0 |
|  |  |  |  | (mm) |  |  |

EXAMPLE 2

As to Emulsions A and B of Example 1, a microbe inhibiting test in a soil was conducted. Cucumber seedlings with developed fifth leaves were transplanted in a contaminated soil with Fusarium oxysporum f cucumerinum to prepare four areas with three repetitions (total twelve spots), i.e. Emulsion A Area, Emulsion B Area, Benomyl Area and Non-treated Area. The contaminated soil contained Fusarium microbes in a proportion of $10^5$ per 1 g of the dry soil.

Immediately after the transplantation, each of the emulsions with components concentration adjusted to 400 ppm was irrigated into the soil in a rate of 3000 ml per m$^2$ to give pots with a diameter of 10 cm and subjected to examination of affected seedlings after 30 days, thus obtaining results shown in Table 3. As apparent from Table 3, in the case of the antioxidant-free Emulsion B, the microbe inhibiting effect was greatly lowered, while in the case of Emulsion A according to the present invention, the microbe inhibiting effect was maintained even after 30 days:

TABLE 3

Pot Test Results on Cucumber with Cinnamic Aldehyde Emulsions A and B

| Reagents | Concentration (Components) | Test Seedlings | Affected Seedlings | Affection Percent | Chemical Damage |
|---|---|---|---|---|---|
| Emulsion A | 400 ppm | 12 | 0 | 0% | — |
| Emulsion B | 400 ppm | 12 | 3 | 25% | — |
| Benomyl Compound | 500 ppm | 12 | 1 | 8% | — |
| Non-treated | — | 12 | 12 | 100% | — |

EXPERIMENT 2

In this experiment, fine powder of white carbon (commercial name, Tokusil N, manufactured by Tokuyama Soda Co., Ltd.) was used as a support. Preparation of a sample was carried out by charging a polyethylene bag having a volume of 1000 ml with 10 g of white carbon and 10 g of cinnamic aldehyde (purity: 98.1%) mixed with a predetermined quantity of an antioxidant and mixing them adequately. On the other hand, a control sample was prepared by similarly adsorbing 10 g of cinnamic aldehyde on 10 g of white carbon.

Each of the thus prepared samples in an amount of 20 g was charged in a wide-mouthed transparent bottle of polyethylene with a volume of 1000 ml and allowed to stand in an open thermostat maintained at 40° C. for 14 days, during which the bottle was shaken several times a day so as to bring the sample in the bottle into uniform contact with the air. After 14 days, 3 g of the sample was weighed, subjected to extraction with 100 ml of ether by means of a Soxhlet extractor, treated with diazomethane after distilling off the ether, and then subjected to methyl-esterification of cinnamic acid, which was then determined quantitatively by gas chromatography. The results are shown in Table 4.

It is apparent from the results of Table 4 that eugenol has a higher oxidation inhibiting effect, but Vitamin-E 80 and EG-5DX (commercial name, manufactured by Nippon Yushi Co., Ltd., composition: vitamin-E 30%, ethyl alcohol 15%, vitamin-C 0.1%, plant fats and oils, gallaic acid 54.9%) has little effect.

TABLE 4

Oxidation Inhibiting Effect of Cinnamic Aldehyde Composition of Solid Type

| Antioxidant | Amount | Cinnamic Aldehyde | Cinnamic Acid |
|---|---|---|---|
| Control | — | 4.16% | 67.05% |
| Eugenol | 1% | 92.67% | 2.05% |
| " | 3% | 90.61% | 1.25% |
| EG-5DX | 1% | 9.84% | 64.09% |
| " | 2% | 3.15% | 61.61% |
| Vitamin-E 80 | 1% | 9.84% | 64.09% |

The following experiment was carried out to examine how nematodes living in the soil are affected by a composition comprising cinnamic aldehyde and eugenol, as an antioxidant, in a proportion of 1%, adsorbed on white carbon, and another composition comprising cinnamic aldehyde adsorbed on white carbon. As the nematode, there were chosen Meloidogyne incognita and Steinernema feltise. The former is a noxious insect greatly damaging crops and the latter is a non-toxic self-supporting nematode. As well known in the art, such a well balance in the soil serves to protect the roots of crops that the density of the former is small and that of the latter is large.

EXPERIMENT 3

A powdered composition comprising cinnamic aldehyde adsorbed on white carbon was divided into four areas with cinnamic aldehyde concentrations of 125 ppm, 250 ppm, 500 ppm and 1000 ppm with provision of a control area free from cinnamic aldehyde.

100 nematodes of Meloidogyne incognita were immersed in aqueous dispersion of these compositions for 1 hour, washed with distilled water and then immersed in distilled water for 24 hours. Then, the number of the surviving ones was examined to give the following results:

| Concentration Area | Surviving Nematodes |
|---|---|
| 125 ppm area | 90 |
| 250 ppm area | 69 |
| 500 ppm area | 0 |
| 1000 ppm area | 0 |
| Control area | 98 |

When the above procedure was repeated except adding 1% of eugenol to the cinnamic aldehyde, the following results were obtained:

| Concentration Area | Surviving Nematodes |
|---|---|
| 125 ppm area | 90 |
| 250 ppm area | 58 |
| 500 ppm area | 0 |
| 1000 ppm area | 0 |

EXAMPLES 3 and 4

The following tests were carried out to known the effects in the soil for a long time.

In a nematode soil test A (Example 3), three samples were prepared by adding 1% by weight of eugenol to cinnamic aldehyde and allowing to adsorb on white carbon respectively to give concentrations of 20%, 33% and 66% by weight. 8 g of each of the thus resulting samples was added to 400 ml of water to form a suspension, and irrigated in 10 l of a soil contaminated with Meloidogyne incognita so as to constantly maintain a soil humidity of 30%, thus providing four test areas including a non-added control area, as shown in Table 5.

In a nematode soil test B (Example 4), three comparative samples were prepared by allowing cinnamic aldehyde to adsorb on white carbon respectively to give concentrations of 20%, 33% and 66% by weight and then applied to the soil in the similar manner to described above, thus providing four test areas including a non-added control area, as shown in Table 6.

In both the tests, the number of *Meloidogyne incognita* and *Steinernema feltiae* was examined after 4 days and 30 days by Baermann funnel method and consequently, it was found that in Tests A and B, there were no significant differences among the test areas after 4 days, but in the examination after 30 days, the samples containing eugenol in addition to cinnamic aldehyde in Test A gave apparently more excellent effects.

In Tables 5 and 6, M represents *Meloidogyne incognita* and S represents *Steinernema feltiae*.

TABLE 5

Nematode Soil Test A Cinnamic Aldehyde + Eugenol + White Carbon

| Cinnamic Aldehyde Concentration | Nematode | No. 1 | No. 2 | No. 3 | No. 4 | Total | Average |
|---|---|---|---|---|---|---|---|
| Four Days | | | | | | | |
| Control | M | 162 | 163 | 124 | 76 | 525 | 131.25 |
|  | S | 219 | 106 | 106 | 128 | 559 | 139.75 |
| 20% | M | 0 | 8 | 16 | 5 | 29 | 7.25 |
|  | S | 458 | 405 | 468 | 177 | 1508 | 377.0 |
| 33% | M | 2 | 0 | 3 | 3 | 8 | 2.0 |
|  | S | 143 | 158 | 206 | 120 | 627 | 156.75 |
| 66% | M | 0 | 2 | 0 | 0 | 2 | 0.5 |
|  | S | 42 | 58 | 41 | 97 | 258 | 64.5 |
| Thirty Days | | | | | | | |
| Control | M | 24 | 7 | 11 | 6 | 48 | 12.0 |
|  | S | 173 | 96 | 77 | 81 | 427 | 106.75 |
| 20% | M | 2 | 2 | 1 | 3 | 8 | 2.0 |
|  | S | 202 | 181 | 131 | 231 | 750 | 187.5 |
| 33% | M | 0 | 0 | 0 | 1 | 1 | 0.25 |
|  | S | 142 | 154 | 152 | 217 | 665 | 166.25 |
| 66% | M | 0 | 0 | 0 | 0 | 0 | 0 |
|  | S | 258 | 31 | 116 | 66 | 471 | 117.75 |

TABLE 6

| Cinnamic Aldehyde Concentration | Nematode | No. 1 | No. 2 | No. 3 | No. 4 | Total | Average |
|---|---|---|---|---|---|---|---|
| Four Days | | | | | | | |
| Control | M | 361 | 266 | 108 | 120 | 855 | 213.55 |
|  | S | 416 | 384 | 193 | 209 | 1202 | 300.5 |
| 20% | M | 109 | 206 | 250 | 166 | 731 | 182.75 |
|  | S | 347 | 487 | 735 | 544 | 2112 | 528.0 |
| 33% | M | 113 | 186 | 120 | 169 | 678 | 169.5 |
|  | S | 324 | 617 | 707 | 528 | 2176 | 544.0 |
| 66% | M | 203 | 288 | 270 | 175 | 936 | 234.0 |
|  | S | 449 | 630 | 599 | 350 | 2028 | 507.0 |
| Thirty Days | | | | | | | |
| Control | M | 55 | 41 | 20 | 186 | 302 | 75.5 |
|  | S | 123 | 94 | 65 | 111 | 393 | 98.25 |
| 20% | M | 451 | 54 | 47 | 50 | 602 | 150.5 |
|  | S | 101 | 114 | 93 | 106 | 414 | 103.5 |
| 33% | M | 118 | 128 | 66 | 47 | 359 | 89.75 |
|  | S | 131 | 206 | 98 | 79 | 514 | 128.5 |
| 66% | M | 1095 | 684 | 828 | 219 | 2826 | 706.5 |
|  | S | 175 | 242 | 200 | 60 | 677 | 169.25 |

It is known that eugenol has an oxidation inhibiting effect. However, there have been published no literatures as to how much eugenol or other antioxidants are to be added to cinnamic aldehyde in order to inhibit the oxidation of cinnamic aldehyde and to maintain the intrinsic microbe inhibiting effect.

The inventor has a number of tests so as to solve the above described problem and consequently, have found that addition of antioxidants, in particular, eugenol in a proportion of 1 to 5% by weight to cinnamic aldehyde results in inhibition of the oxidation of cinnamic aldehyde, but with the increase of the addition quantity thereof in the range of more than 1% by weight, the microbe inhibiting effect is rather deteriorated. This is a completely unexpected result, because it has hitherto been reported that the phenol coefficients for gramposi- tive microbes fluctuate to some extent depending upon analyzers, but there is not a large difference in microbe inhibiting effect. That is, cinnamic aldehyde gives a microbe inhibiting effect of 17, while eugenol, 15 ((1) A. R. Penfold: "Perfume and Essential Oil Report" 15, p 388 (1925)), cinnamic aldehyde gives a microbe inhibit- ing effect of 3.0, while eugenol gives that of 8.5 ((2) S. Lideal: ibid, 19, p 285 (1928)) and cinnamic aldehyde gives a microbe inhibiting effect of 8.8 while eugenol gives that of 14.4 ((3) H. Flueller: "Seifen Ehre Fette Wachse" 98 p 677 (1972)).

The inventor has made examinations on methods of protecting plants, in particular, crops. Thus, it is found that there is a remarkable difference with respect to the inhibiting effect of gram-negative microbes which dam- age crops between cinnamic aldehyde and eugenol and the eugenol to cinnamic aldehyde ratio of the microbe inhibiting effect is in the range of 1/5 to 1/10. That is, the microbe inhibiting action or effect against gram- negative microbes is completely unexpected from the microbe inhibiting action or effect against gram-positive microbes, as described in the above literatures (1) to (3). In both of a Schale test in a room (Experiment 4) and a pot test using cucumber (Experiment 5), the microbe inhibiting effect is relatively lowered with the increase of the amount of eugenol.

EXPERIMENT 4 (SCHALE TEST)

To 60 g of white carbon were added cinnamic alde- hyde and eugenol in proportions as shown in the fol- lowing table to prepare seven sample compositions differing in concentration. As microbes to be tested, five popular microbes which attack crops were chosen and subjected to testing by preparing PSA culture media from the sample compositions to give cinnamic alde- hyde concentrations of 25, 50, 100 and 200 ppm. The microbe inhibiting effects were compared by the grown diameters of mycelial colony. Using a Schale with a diameter of 70 mm, the data of 70 mm means that the Schale was full of the mycelial colony. Data obtained by determining three days and five days after inocula- tion of the microbes for check are shown in Table 7.

(1) Sample Compositions (weight ratio)

|  | Cinnamic Aldehyde | Eugenol | Eugenol/Cinnamic Aldehyde Ratio (wt %) | White Carbon |
|---|---|---|---|---|
| TE-1 | 39.6 | 0.4 | 1 | 60 |
| TE-2 | 39.2 | 0.8 | 2 | 60 |
| TE-5 | 38.0 | 2.0 | 5.2 | 60 |
| TE-10 | 36.0 | 4.0 | 11 | 60 |
| TE-20 | 32.0 | 8.0 | 25 | 60 |
| TE-40 | 24.0 | 16.0 | 66 | 60 |
| TE-50 | 20.0 | 20.0 | 100 | 60 |

(2) Microbes Tested

*Fusarium oxysporum f. cucumerinum, Pythium debaryanum, Botrytis cinerea, Rhizoctonia solani, Colleto- trichum lagenarium.*

(3) Concentrations Tested
25, 50, 100 and 200 ppm.
(4) Test Method
Testing on PSA plate medium.

TABLE 7

| | | Microbes | | | | | | | | | |
|---|---|---|---|---|---|---|---|---|---|---|---|
| | Conc. | 3 Days | | | | | 5 days | | | | |
| | (ppm) | I | II | III | IV | V | I | II | III | IV | V |
| TE-1 | 25 | 20 | 70 | 68 | 37 | 62 | 54 | 70 | 70 | 65 | 70 |
| | 50 | 10 | 70 | 50 | 34 | 57 | 46 | 70 | 70 | 63 | 70 |
| | 100 | 0 | 70 | 15 | 32 | 47 | 40 | 70 | 65 | 53 | 70 |
| | 200 | 0 | 0 | 0 | 0 | 0 | 0 | 0 | 0 | 0 | 0 |
| TE-2 | 25 | 20 | 70 | 68 | 38 | 62 | 55 | 70 | 70 | 65 | 70 |
| | 50 | 10 | 70 | 50 | 36 | 57 | 48 | 70 | 70 | 63 | 70 |
| | 100 | 5 | 70 | 17 | 32 | 48 | 40 | 70 | 68 | 54 | 70 |
| | 200 | 0 | 0 | 0 | 0 | 0 | 0 | 0 | 0 | 0 | 0 |
| TE-5 | 25 | 22 | 70 | 68 | 40 | 63 | 58 | 70 | 70 | 66 | 70 |
| | 50 | 8 | 70 | 55 | 37 | 59 | 50 | 70 | 70 | 63 | 70 |
| | 100 | 5 | 70 | 20 | 33 | 53 | 41 | 70 | 70 | 57 | 70 |
| | 200 | 0 | 0 | 0 | 0 | 0 | 0 | 0 | 0 | 0 | 0 |
| TE-10 | 25 | 30 | 70 | 70 | 40 | 63 | 60 | 70 | 70 | 65 | 70 |
| | 50 | 25 | 70 | 70 | 38 | 60 | 53 | 70 | 70 | 64 | 70 |
| | 100 | 13 | 70 | 50 | 37 | 48 | 45 | 70 | 70 | 59 | 70 |
| | 200 | 10 | 8 | 10 | 10 | 5 | 20 | 40 | 60 | 40 | 60 |
| TE-20 | 25 | 39 | 70 | 70 | 40 | 63 | 60 | 70 | 70 | 66 | 70 |
| | 50 | 35 | 70 | 70 | 38 | 60 | 56 | 70 | 70 | 65 | 70 |
| | 100 | 30 | 70 | 70 | 37 | 50 | 50 | 70 | 70 | 63 | 70 |
| | 200 | 23 | 15 | 15 | 20 | 40 | 45 | 60 | 68 | 45 | 67 |
| TE-40 | 25 | 40 | 70 | 70 | 40 | 64 | 63 | 70 | 70 | 66 | 70 |
| | 50 | 38 | 70 | 70 | 37 | 62 | 60 | 70 | 70 | 66 | 70 |
| | 100 | 34 | 70 | 70 | 37 | 55 | 57 | 70 | 70 | 64 | 70 |
| | 200 | 26 | 30 | 17 | 33 | 47 | 52 | 70 | 70 | 52 | 70 |
| TB-50 | 25 | 42 | 70 | 70 | 42 | 64 | 65 | 70 | 70 | 66 | 70 |
| | 50 | 40 | 70 | 70 | 38 | 62 | 60 | 70 | 70 | 65 | 70 |
| | 100 | 38 | 70 | 70 | 37 | 55 | 58 | 70 | 70 | 62 | 70 |
| | 200 | 30 | 60 | 20 | 34 | 48 | 55 | 70 | 70 | 53 | 70 |
| | 0 | 43 | 70 | 70 | 42 | 64 | 69 | 70 | 70 | 66 | 70 |

Note:
I: Fusarium,
II: Pythium;
III: Rhizoctonia;
IV: Colletotrichum;
V: Botrytis

EXPERIMENT 5 (POT TESTS A AND B)

Using the same sample compositions as used in Ex- periment 4, pot tests were carried out on soil pathogenic microbes, i.e. Pythium and Fusarium. Dilution of the sample composition was 1000 times and cucumber (Tokiwa Hikari No. 3, P-type) was used as an object crop. That is, a soil contaminated with each of the pathogenic microbes was charged in in a 1/5000 are Wagner pot and immediately after seeding a germinat- ing seed of cucumber therein, the each sample composi- tion was irrigated at a rate of 3000 ml/m$^2$, after which the same amount thereof was irrigated every 10 days and examination was conducted 30 days after seeding, thus obtaining results shown in Tables 8 and 9. In any of the test areas, better results are obtained in the case of adding eugenol in a proportion of 1 to 5% by weight to cinnamic aldehyde and the effect of eugenol is rather lowered with the further increase of the amount thereof.

TABLE 8

| | Results of Pot Test A (Fusarium) | | | |
|---|---|---|---|---|
| Sample Composition | Multiple of Dilution | Seedlings Tested | Seedlings Affected | Seedlings Affected (%) |
| TE-1 | 1000 | 50 | 0 | 0 |
| TE-2 | 1000 | 50 | 0 | 0 |
| TE-5 | 1000 | 50 | 1 | 2 |
| TE-10 | 1000 | 50 | 10 | 20 |
| TE-20 | 1000 | 50 | 19 | 38 |
| TE-40 | 1000 | 50 | 27 | 54 |
| TE-50 | 1000 | 50 | 30 | 60 |
| Non-treated | — | 50 | 35 | 70 |

TABLE 9

| | Results of Pot Test B (Pythium) | | |
|---|---|---|---|
| Sample Composition | Multiple of Dilution | Seedlings Tested | Seedlings Affected | Seedlings Affected (%) |
| TE-1 | 1000 | 50 | 0 | 0 |
| TE-2 | 1000 | 50 | 0 | 0 |
| TE-5 | 1000 | 50 | 0 | 0 |
| TE-10 | 1000 | 50 | 5 | 10 |
| TE-20 | 1000 | 50 | 18 | 36 |
| TE-40 | 1000 | 50 | 33 | 66 |
| TE-50 | 1000 | 50 | 41 | 82 |
| Non-treated | — | 50 | 46 | 92 |

EXAMPLE 5

Using a cinnamic aldehyde wettable powder of the present invention comprising 39.6% by weight of cinnamic aldehyde, 0.4% by weight of eugenol and 60.0% by weight of white carbon (referred hereinafter to as TM wettable powder), a test on the scab of Japanese apricot was carried out by the following test method, thus obtaining results as shown in Table 10. It is apparent from this result that the TM wettable powder diluted with a multiple of 100 times gives a more excellent insect exterminating effect than a control composition without affecting leaves and fruits.

TEST METHOD

Test Place: Miyakawauchi, Donaricho, Edanogun
Kind and Tree Age: Uguisu Yado, 7 years
Scale of Test: one tree per one plot and four replication
Diseases and insects for check: somewhat many
Spraying Before Test: no
Treatment Time, Amount and Method: A sufficient amount of the wettable powder was sprayed by means of a power sprayer in such a manner that the liquid fell in drops four times on April 28, May 9, May 20 and May 27.
Weather during Testing Peiord: The atmospheric temperature from April to May was higher than the normal year. The rainfall during the same period was more than the normal year.
Examination Date and Method: The examination was conducted June 3, 1986 as to whether there had occurred disease of 200 fruits per one tree and damages from the chemicals.

TABLE 10

| | Results of Test on Scab of Japanese Apricot | | | | | |
|---|---|---|---|---|---|---|
| | | Concentration | | Fruits | | Damage | |
| Sample Composition | Content (%) | Dilution Multiple | Effective Content (ppm) | Number Examined | Disease Ratio (%) | by Chemicals (%) | Utility |
| Present Invention | | | | | | | |
| TM Wettable Powder | 40 | 500 | 800 | 800 | 4.0 | — | yes |
| For Comparison | | | | | | | |
| Topzine M Wettable Powder | 70 | 1500 | 467 | 800 | 6.7 | — | |
| Blank | | | | | | | |
| No Spraying | | | | | 850 | 51.6 | |

The preceding examples and experiments are in no way to be construed as limiting the scope of the present invention, these specific embodiments being presented simply to exemplify the best mode of operation of the disclosed method.

It will clearly be understood from the above described examples and experiments that according to the method of protecting crops of the present invention, there can be obtained following advantages or merits. That is, the use of a non-toxic and stable composition comprising non-toxic and harmless cinnamic aldehyde and an antioxidant results in a selectively strong microbe inhibiting effect against, in particular, pathogenic microbes or molds in the soil without having no influences upon useful microorganisms, and in a breeding effect of harmless nematoda, for example, *Steinernema feltiae* in spite of inhibiting noxious *Meloidogyne incognita*. This is a more excellent method of protecting crops, whereby the antibiosis by microorganism can effectively be utilized so as to advantage protection of crops and such effects as described above can stably be maintained by the presence of an antioxidant. Furthermore, this method serves to improve the soils without unfavorably affecting the human body and environment and is advantageous from an economical point of view.

What is claimed is:

1. A method of protecting crops against attack by insects, pathogenic fungi, or bacteria which comprises applying or spraying an insecticidally effective amount, a fungicidally effective amount, or a bactericidal effective amount of a composition comprising cinnamic aldehyde and an antioxidant on crops.

2. The method as claimed in claim 1, wherein the composition further contains an emulsifier.

3. The method as claimed in claim 1, wherein the composition is supported on a support.

4. The method as claimed in claim 1, wherein the antioxidant is at least one selected from the group consisting of vitamin E, n-propyl gallate, BHT and eugenol.

5. The method as claimed in claim 1, wherein the antioxidant is in a proportion of 0.2 to 1% by weight to the cinnamic aldehyde.

6. The method as claimed in claim 2, wherein the emulsifier is at least one selected from the group consisting of fatty acid salts, higher alcohol sulfuric acid esters, alkylallylsulfonates, polyoxyethylene alkyl ethers, polyoxyethylene alkylpheno ethers, polyoxyethylene alkyl esters, polyoxyethylene sorbitan alkyl esters, sorbitan alkyl esters, aliphatic amino salts, quaternary ammonium salts and alkylpyridinum salts.

7. The method as claimed in claim 1, wherein the composition comprises 5 to 50% by weight of cinnamic aldehyde, 0.01 to 0.5% by weight of an antioxidant, 0.5 to 10% of an emulsifier and the balance of water.

8. The method as claimed in claim 3, wherein the support is of a material selected from the group consisting of calcium oxide, silicon oxide, magnesium oxide, aluminum oxide, montmorillonite, bentonite, zeolite, white carbon and calcium silicate.

9. The method as claimed in claim 3, wherein cinnamic aldehyde is supported on the support in a proportion of 5 to 50% by weight.

10. A method for selectively killing Meloidogyne incognita, in the presence of *Steinernema feltiae* in soil, by applying to soil a *Meloidogyne incognita* pesticidally effective amount of a composition comprising cinnamic aldehyde and an antioxidant.

11. The method of claim 10 wherein said composition is applied to the soil in amounts of 125 ppm to 1,000 ppm per area.

* * * * *